(12) United States Patent
Wright

(10) Patent No.: US 8,678,010 B2
(45) Date of Patent: Mar. 25, 2014

(54) MOUTHGUARD WITH MAGNETIC TETHERING

(75) Inventor: Michael Duane Wright, Sandy Spring, MD (US)

(73) Assignee: The Wright Guard, Bethesda, MD (US)

( * ) Notice: Subject to any disclaimer, the term of this patent is extended or adjusted under 35 U.S.C. 154(b) by 286 days.

(21) Appl. No.: 13/372,062

(22) Filed: Feb. 13, 2012

(65) Prior Publication Data

US 2012/0285473 A1    Nov. 15, 2012

Related U.S. Application Data

(60) Provisional application No. 61/485,999, filed on May 13, 2011.

(51) Int. Cl.
  *A61C 5/14*    (2006.01)
(52) U.S. Cl.
  USPC .......................................... 128/859; 128/862
(58) Field of Classification Search
  USPC ................ 128/848, 859–862; 602/902; 433/6
  See application file for complete search history.

(56) References Cited

U.S. PATENT DOCUMENTS

| | | | |
|---|---|---|---|
| 2,705,492 A * | 4/1955 | Chandler | 128/862 |
| 3,319,626 A | 5/1967 | Lindsay | |
| 3,457,916 A | 7/1969 | Wolicki | |
| 3,496,936 A | 2/1970 | Gores | |
| 5,117,816 A * | 6/1992 | Shapiro et al. | 128/200.24 |
| 5,339,832 A | 8/1994 | Kittelsen et al. | |
| 6,536,424 B2 * | 3/2003 | Fitton | 128/200.24 |
| 7,156,774 B2 * | 1/2007 | Mohindra | 482/11 |
| 7,404,403 B2 * | 7/2008 | Farrell | 128/859 |
| 7,637,262 B2 * | 12/2009 | Bailey | 128/848 |
| 2004/0250817 A1 | 12/2004 | Kittelsen et al. | |
| 2006/0065277 A1 | 3/2006 | Jacobs | |
| 2006/0150304 A1 | 7/2006 | Bentz | |
| 2008/0199824 A1 | 8/2008 | Hargadon | |
| 2010/0122402 A1 | 5/2010 | Tipp | |
| 2011/0091833 A1 | 4/2011 | Farrell | |
| 2011/0155146 A1 | 6/2011 | Marsh | |

OTHER PUBLICATIONS

Intl. Search Report/Written dated Oct. 18, 2012 of PCT/US12/37654 filed May 11, 2012 (11 pages).

* cited by examiner

*Primary Examiner* — Michael A. Brown

(57) ABSTRACT

A dual layer mouthguard with a U-shape polycarbonate/EVA or elastomeric material skeletal base includes channels and ramps to ensure a uniform thickness on the occlusal, buccal and lingual surfaces of the teeth for proper alignment of the jaw and positioning for protection during the placement of the mouthguard. The liner is softer than the base when introduced to heat and remains softer as it is cooled. The base may also include metal/magnetic insertion to serve as a tethering device for temporary storage.

32 Claims, 21 Drawing Sheets

TOP VIEW

PERSPECTIVE VIEW

FRONT VIEW

BOTTOM VIEW

REAR VIEW

CROSS-SECTION VIEW

MOUTHGUARD WITH MAGNETIC TETHERING

CROSS-REFERENCE TO RELATED APPLICATION

This application claims benefit under 35 USC 119(e) to copending U.S. provisional application Ser. No. 61/485,999, filed on May 13, 2011, the entire contents of which are incorporated herein by reference.

BACKGROUND

This application is directed to protective mouthguards for use by athletes to ensure proper placement of the device and jaw alignment, dissipation of detrimental forces during activity, and temporary storage of the mouthguard.

Historically, mouthguard tethering devices consisted of nylon or thermoplastic material that connects the sports guard to the face mask of the helmet. This outdated design is not favored by athletes because it is cumbersome, swings about freely, and places the athlete at risk for head and/or neck injuries when the facemask is incidentally grasped during competition.

Mouthguards are designed to protect the athlete during play by reducing the impact forces to the player during competition. However, failing to wear a mouthguard or wearing an ill fitted device can cause detrimental short term and long term effects such as tooth fracture, tooth avulsion/luxation, condylar and/or mandible fracture, maxillary fracture, jaw fractures, migraines, concussions and TMJ disorders.

Currently, two types of mouthguards exist on the market—custom fit and non-custom fit. Custom fit mouthguards generally provide the best protection for athletes, but are expensive and require a dentist for proper fabrication and fitting. The athlete's molds are made by taking impressions of the maxillary and mandibular teeth. A bite registration is recorded using a wax or elastomeric material. This registers the athlete's jaw position and how the teeth interdigitate. This record is then used to ensure that the upper and lower teeth are properly aligned, and a thermoplastic material is placed over one of the arches to serve as the mouthguard. The prosthesis is then trimmed to ensure proper fit and comfort, and the occlusion is registered by reheating the thermoplastic material to ensure the teeth and condyle are in a protected position. Due to the expense and need for a dental professional to fit custom mouthguards, many athletes do not avail themselves of the added protection and superior performance provided by custom fitting.

So-called "boil and bite" conventional mouthguards are examples of non-custom fit "off the shelf" protective devices widely available on the market. Today's "boil and bite" mouthguards offer little protection to players and are inadequate in various areas including fit, impact strength, proper teeth and jaw positioning, temporary storability, and debonding of the softer layer from the more rigid harder core. Stock mouthguards can be made of rubber, polyvinyl chloride, or a polyvinyl acetate copolymer, and are available in small, medium and large sizes. These conventional mouthguards are not custom molded to fit the individual, and exhibit inadequate support, retention and stability, resulting in common complaints by the user.

Non custom mouthguards such as the "boil and bite" are often ill-fitting and, if not properly seated during the forming phase after heating, can cause injury. One limitation of the "boil and bite" is the inability to provide a uniform thickness around the anterior and posterior teeth for protection. A thickened area of material in one area can cause distortion when cooled, and can become very thin areas in others. These thin areas can lead to inadequate thickness for protection and resulting injury.

Another problem with conventional "boil and bites" is the inability of the user to ensure proper placement of the guard and proper positioning of the jaw during fabrication and fitting. By placing the tray too far anteriorly, posteriorly, or laterally, the teeth are not adequately protected because the guard becomes offset. This creates a bulk of material or thinning of material which may lead to distortion or inadequate protection. Improper seating of the mouthguard during setting can also cause the material to be bulky and more importantly, can lead to improper positioning of the jaw. This may result in harmful effects in the temporal mandibular complex.

Other problems exist in conventional mouthpiece designs. For example, the athlete has no adequate place for storage when the device is temporarily removed during activity. In football, for example, the athlete's mouth guard is sometimes tethered to the helmet via the facemask. This common method of storage results in the mouthguard dangling from the player's helmet. This is often unfavorable to the athletes, and more players are simply holding the mouth guard in their hand or wedging it in the facemask. By wedging the mouth guard, the guard becomes distorted which, in turn, effects the fit and protection. By simply holding the guard, it becomes cumbersome and is often lost or dropped. When dropped, the athlete's mouthguard is soiled with dirt and other harmful bacteria which can lead to numerous problems, including health issues. Another reason athletes find the conventional tethering system unfavorable is that it limits their range of motion as they move their heads in different positions. This conventional tethering of the jaw to the helmet can also cause injury when another player grabs the helmet and the head/neck and jaw is abruptly malpositioned. Conventional approaches do not provide a convenient, safe means of affixing a mouth guard to a player's equipment for storage.

What is needed is a mouthguard that can be easily fitted without the assistance of a dentist, while providing superior protection beyond that available from conventional "boil and bites". What is further needed is a mouthguard that lowers the risk of severe injury during activity, allows for the proper placement and alignment of the teeth and jaw structures, and which offers safety and sanitization during periods of non-use. What is also needed is an easy and reliable mouthguard storage mechanism that reduces opportunities for contamination or loss during periods of non-use.

SUMMARY

Among other things, this disclosure provides embodiments of a protective mouthguard with improved fit and protection in comparison to conventional "boil and bite" mouthguards, and with less expense and comparable performance to custom mouthguards crafted by a dentist, for example.

In one or more embodiments, alternative innovative clamps, both using a magnetic material design, are disclosed which secure to the face mask and allows the athlete's mouthguard to be temporarily affixed to a helmet, for example, when not being used. In addition, magnetic material can be used in custom mouthguards as well.

In one or more embodiments, the innovative protective mouthguard design of this disclosure addresses concerns identified above with respect to non-professionally fitted mouthguards. For example, embodiments of this disclosure use specially designed built-in guides and scaffolds at experimentally determined angles and/or heights to ensure proper tooth and jaw positioning for protection of a wide population of users. Accordingly, various embodiments of the protective mouthguard of this disclosure address the problems of fit, comfort, speech, and breathability of conventional "boil and bite" mouthguards. In addition, the innovative protective mouthguard design of this disclosure addresses concerns with the expense of custom fitted mouthguards.

In one embodiment, a dual layer protective mouthguard includes an outer layer comprising an exoskeleton having a generally U-shaped tapered base and inner and outer walls adapted to extend into a vestibular area of an oral cavity of a particular person using the protective mouthguard; an inner layer, e.g., a thermo-plastic flowable material, bonded to the inner wall of the outer layer, wherein the exoskeleton comprises front and rear interior scaffold structures having a predetermined height above a bottom of the U-shaped tapered base selected to contact incisor and molar teeth of a selected population of users using the protective mouthguard so as to ensure a uniform thickness of the inner layer material, e,g., a thermo-plastic flowable material, when the protective mouthguard has been fitted to the particular person in the selected population of users, wherein the exoskeleton further comprises interior tapered side bumpers extending from the interior wall of the exoskeleton, said side bumpers arranged to position the mouthguard within the oral cavity and provide a plurality of contact surfaces located at a contour height suitable for contacting teeth of the selected population of users, said plurality of contact surfaces ensuring a desired flow of the inner layer material around each tooth of the particular person when the mouthguard is being fitted to the particular person and thereby provide a desired protective thickness of the thermo-plastic flowable material after being fitted.

In one or more embodiments, a tethering mechanism is included that provides the ability to avoid contamination of the mouthguard during periods of non-use. In one implementation, a magnetic tether is provided, with magnetic or ferromagnetic material embedded in the mouthguard, with a corresponding magnetic or ferromagnetic receiver suitable for holding the mouthguard on a helmet, wristband, or helmet decal, for example.

In one or more embodiments, preventive technologies such as caries prevention utilizing fluoride and/or calcium phosphate and/or medications may be incorporated into the softer inner layer.

In another embodiment, a method of fitting a protective mouthguard to a particular person having physiological parameters encompassed by a selected population of users includes heating the inner layer; placing the protective mouthguard including the heated inner layer in the oral cavity of the particular person using the protective mouthguard; contacting the front and rear interior scaffold structures with incisor and molar teeth of the particular person and thereby ensuring a uniform thickness of the thermo-plastic flowable material; using the interior tapered side bumpers to position the mouthguard within the oral cavity and thereby provide a plurality of contact surfaces and thereby ensuring a desired flow of the thermo-plastic flowable material around each tooth of the particular person; forming the protective mouthguard to oral structures of the particular person, said interior tapered side bumpers and said front and rear interior scaffold structures ensuring a desired protective thickness of the thermo-plastic flowable material after the heated inner layer has cooled, said interior tapered side bumpers ensuring aligning the mouthguard in the oral cavity such that impact forces are directed over a long axis of each tooth of the particular user.

In another embodiment, a method of fitting a protective mouthguard to a particular person having physiological parameters encompassed by the selected population of users includes obtaining a digitally scanned image of oral structures of the particular person; using the digitally scanned image to form a model of the oral structures; heating the inner layer; preforming the protective mouthguard to a shape of the oral structures by using the model, said interior tapered side bumpers and said front and rear interior scaffold structures ensuring a desired protective thickness of the inner layer material after the heated inner layer has cooled, said interior tapered side bumpers ensuring aligning the mouthguard in the oral cavity such that impact forces are directed over a long axis of each tooth of the particular user.

In another embodiment, a method of making a protective mouthguard suitable for providing protection for persons having oral structure properties encompassed by a population of similarly sized but different persons includes obtaining a plurality of oral scan tracings from persons included in the population; overlaying the plurality of oral scan tracings; determining an average centerline of the plurality of oral scan tracings; determining a maximum and a minimum dimension of the protective mouthguard calculated using the plurality of oral scan tracings; and identifying inside bumper locations for plural interior bumpers, said identified locations ensuring contact with all teeth of persons encompassed in the population.

In another embodiment, a mouthguard tethering system includes an external attachment mechanism comprising a clamp mechanism, wherein said clamp mechanism comprises a first clamp half; a second clamp half; a connector arrangement configured to connect the first clamp half to the second clamp half; a ferrous and/or magnetic disc configured to be received in an opening in the second clamp half; and a protective covering arranged to cover the connector arrangement, the ferrous and/or magnetic disc and the opening in the second clamp half.

These and other features and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In various embodiments of this disclosure, the structural components illustrated herein are drawn to scale. It is to be expressly understood, however, that the drawings are for the purpose of illustration and description only and are not intended as a definition of the limits of the inventive concept. As used in the specification and in the claims, the singular form of "a", "an", and "the" include plural referents unless the context clearly dictates otherwise.

BRIEF DISCUSSION OF THE DRAWINGS

Figure 1:
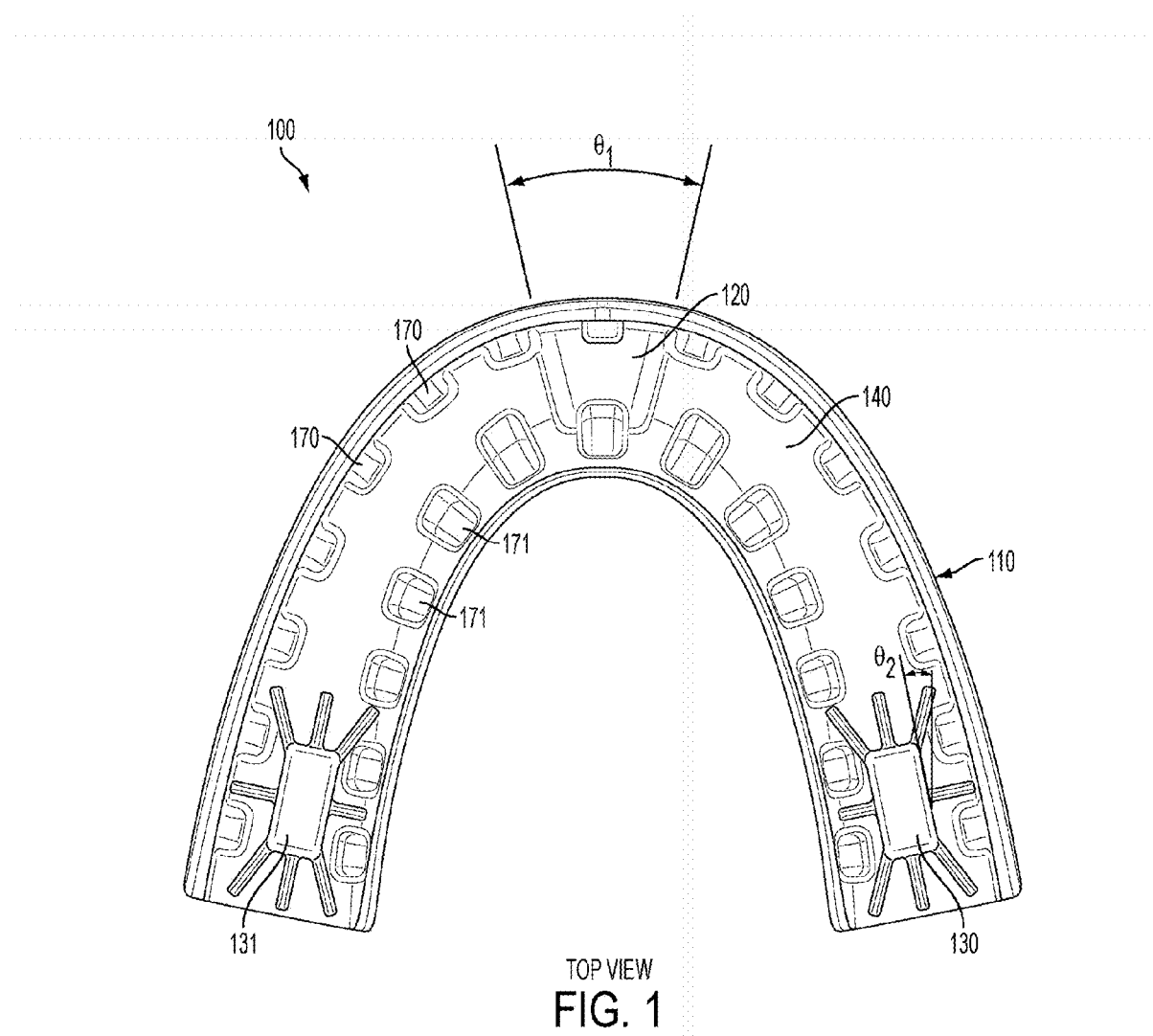
FIG. 1 illustrates a top view of an exoskeleton or outer shell of a mouthguard of an embodiment.
Figure 8:
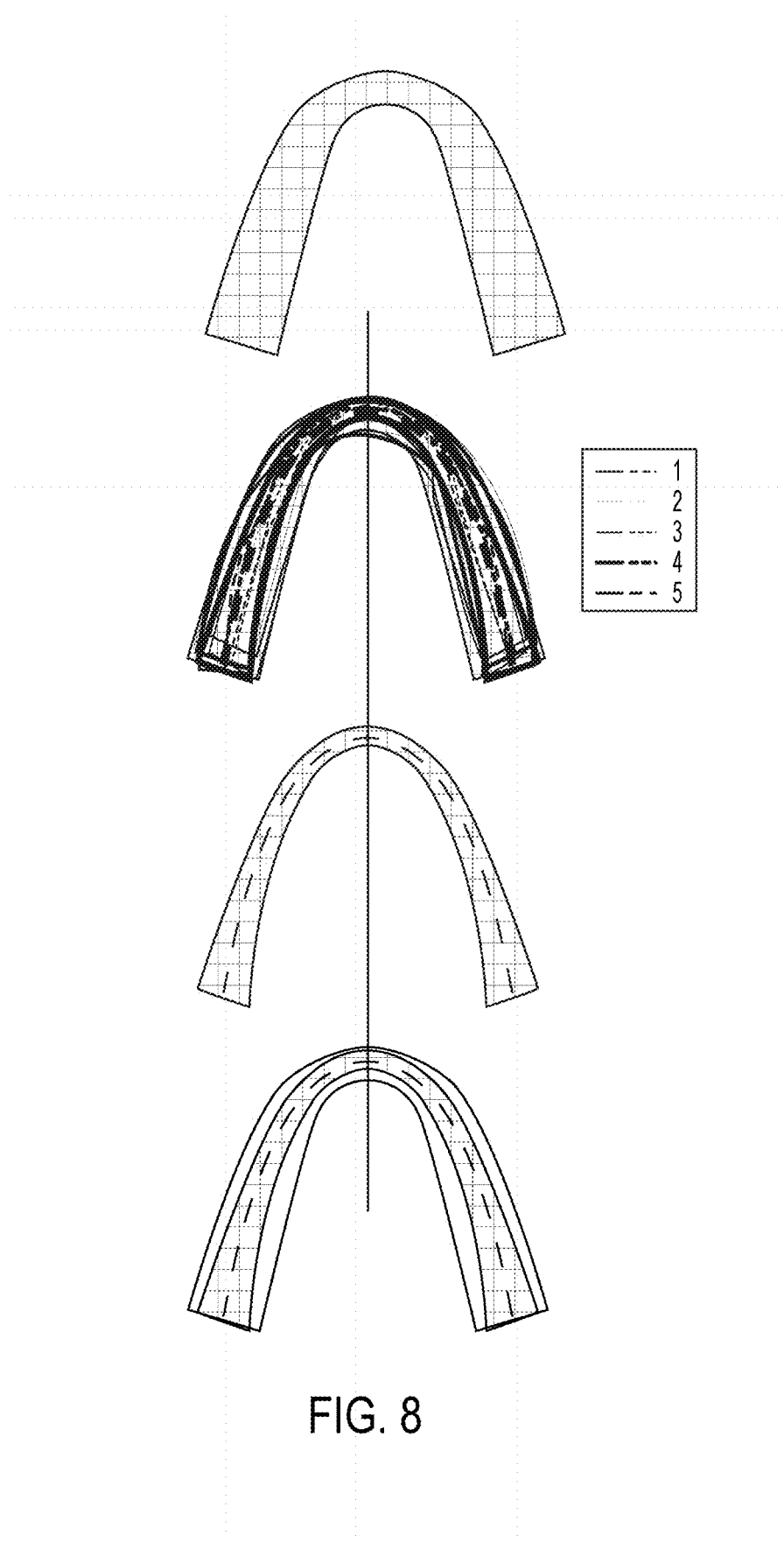
Figure 9:
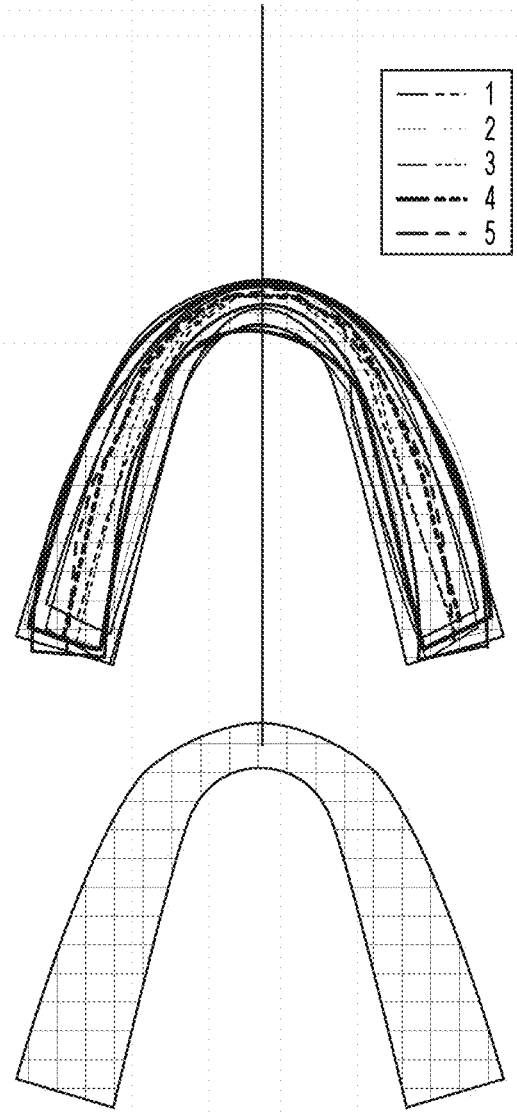
Figure 11:
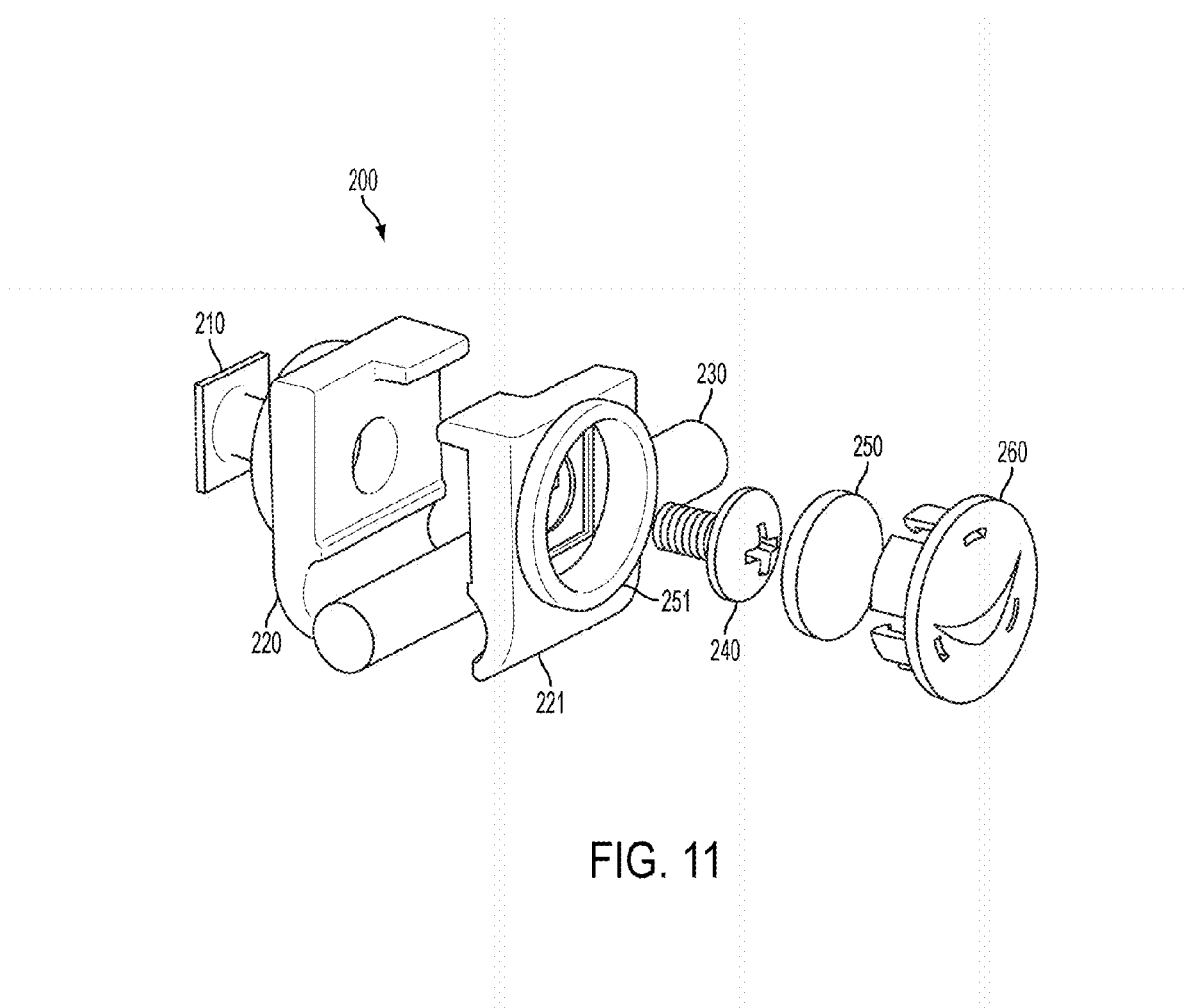
Figure 12A:
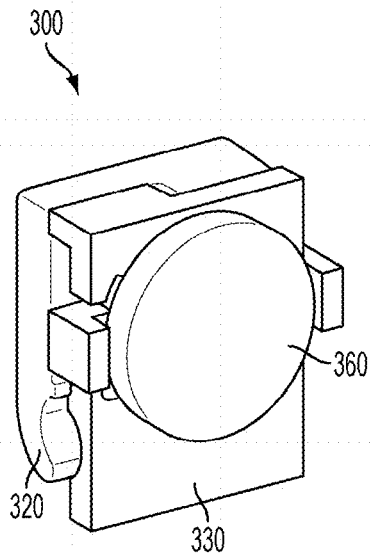
Figure 12B:
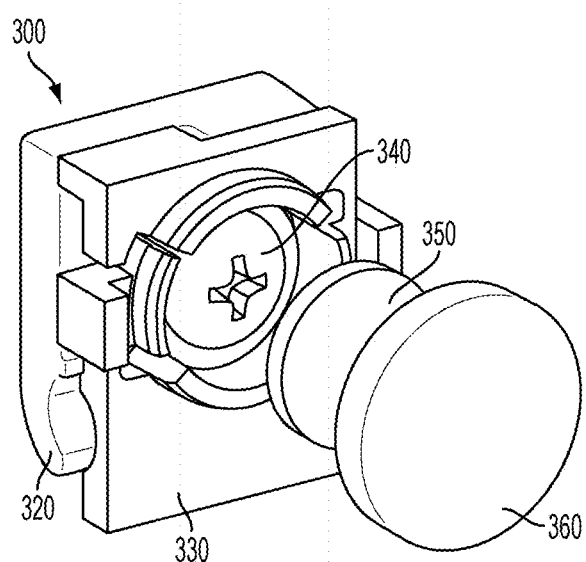
Figure 12C:
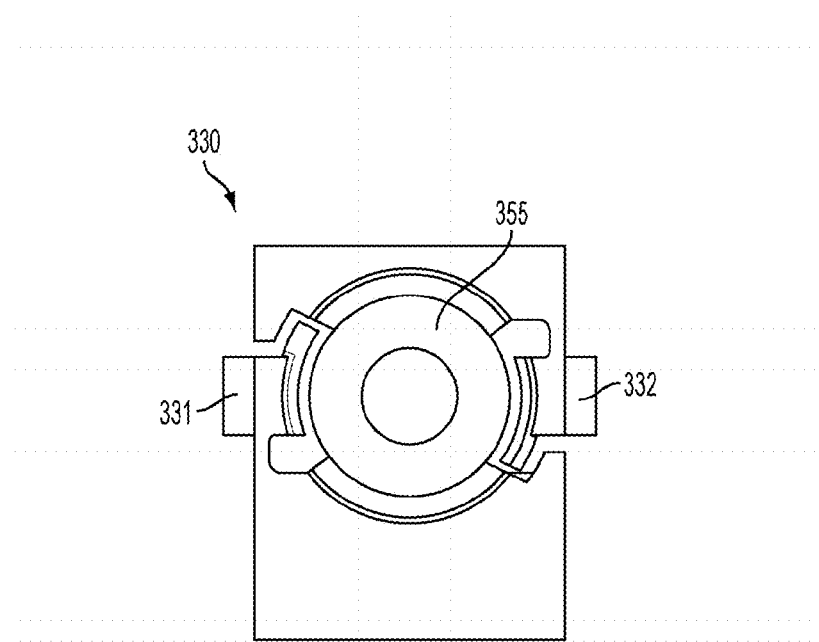
Figure 12D:
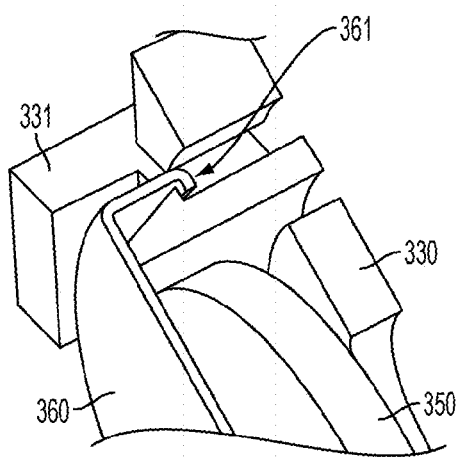
Figure 13A:
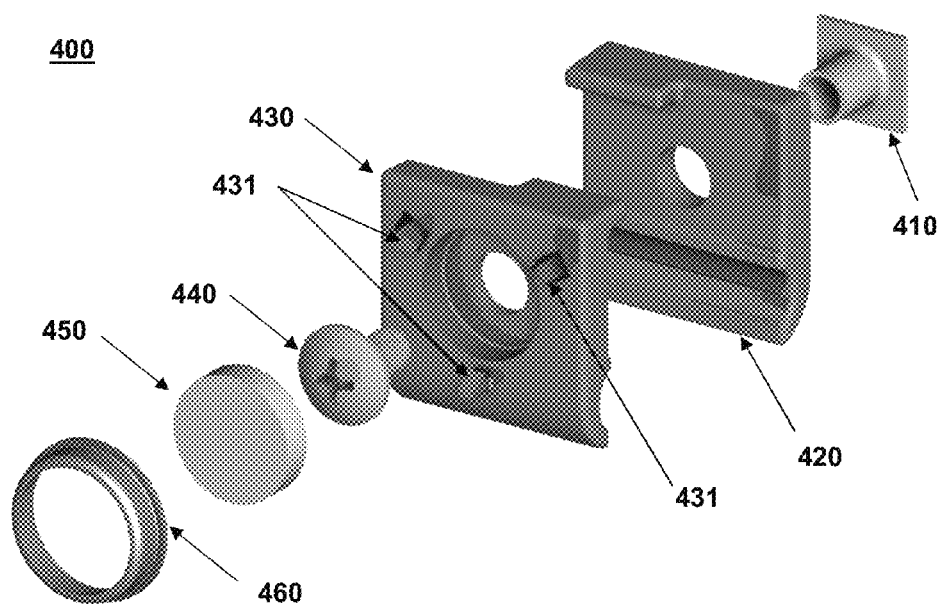
Figure 13B:
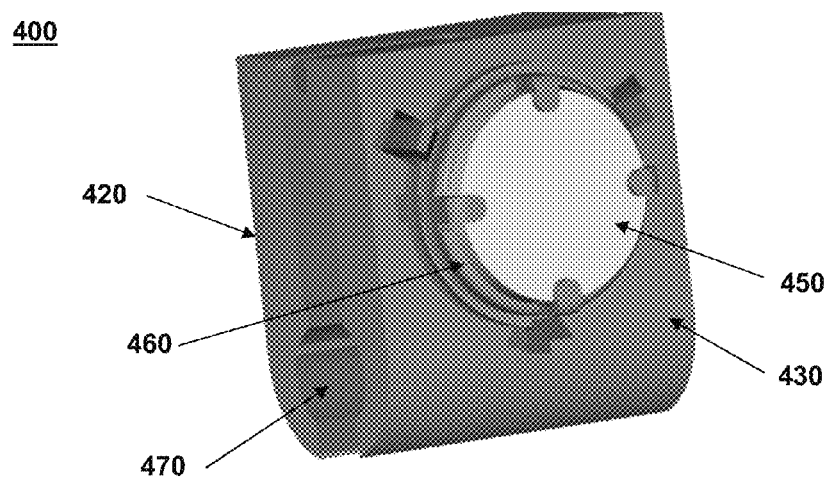

FIG. 8 provides an overlay and evolution of the dimensions of the an embodiment of the exoskeleton of FIG. 1 using the five patient scan tracings of FIGS. 7A-7E;

FIG. 9 illustrates the overlay of the five patient scan tracings of FIGS. 7A-7E to determine the dimensions of an exemplary exoskeleton of an embodiment;

FIGS. 10A-10H illustrate various perspective views of the layered protective mouthguard of an embodiment and which includes an outer layer/exoskeleton of FIG. 1 and an inner thermoplastic layer;

FIG. 11 illustrates an embodiment of a novel mouthguard clamping mechanism;

FIGS. 12A-12D illustrate an alternative embodiment of a novel mouthguard clamping mechanism; and FIGS. 13A-13B illustrate an alternative embodiment of a novel mouthguard clamping mechanism.

DETAILED DESCRIPTION

This disclosure provides, in one or more embodiments, a dual layer mouthguard 100 having a U-shaped tapering base with an inner and outer wall extending into the vestibular area of the oral cavity. The outer and inner framework consists of a light weight, shock absorbing material to protect the teeth, surrounding soft tissue and temporal mandibular complex. The liner material may be a thermo-plastic material, e.g., ethyl vinyl acetate (EVA) material, polyurethane, polystyrene, or selected blends thereof, which may be bonded to the harder outer exoskeleton/core, e.g., mechanically coupled and/or chemically bonded. Alternatively, polystyrene may be used, or a nanocarbon material may be used in forming the inner layer or liner material.

With reference to FIGS. 1-5, advantages of one or more embodiments of new mouthguard design 100 may be found in various features illustrated in the drawings and discussed below. For example, in one embodiment, harder outer core (or exoskeleton) 110 contains front scaffold 120 and rear scaffolds 130, 131 on interior tray portion 140 made of a semi-rigid material on which the molars and incisor teeth will contact during and after initial fitting to ensure a uniform thickness of the softer, liner material 195 that is placed into interior 140 of exoskeleton 110 to fit mouthguard 100 to a particular user. Liner material 195 may be a flowable material, such as polystyrene, polyurethane, or EVA, and may optionally include a reinforcing nanocarbon fiber material. Exoskeleton 110 may be polystyrene, EVA or a polyurethane/EVA blend, and may include a reinforcing nanocarbon fiber material. The softer liner material 195 is not shown in FIGS. 1-6 to aid in exposition of the arrangement of the constituent parts of exoskeleton 110. The material used for the inner layer, e.g., flowable liner material 195 is selected to be strong enough to absorb and dissipate forces so as to reduce traumatic injury to the teeth, TMJ, and surrounding oral structures.

Figure 10A:
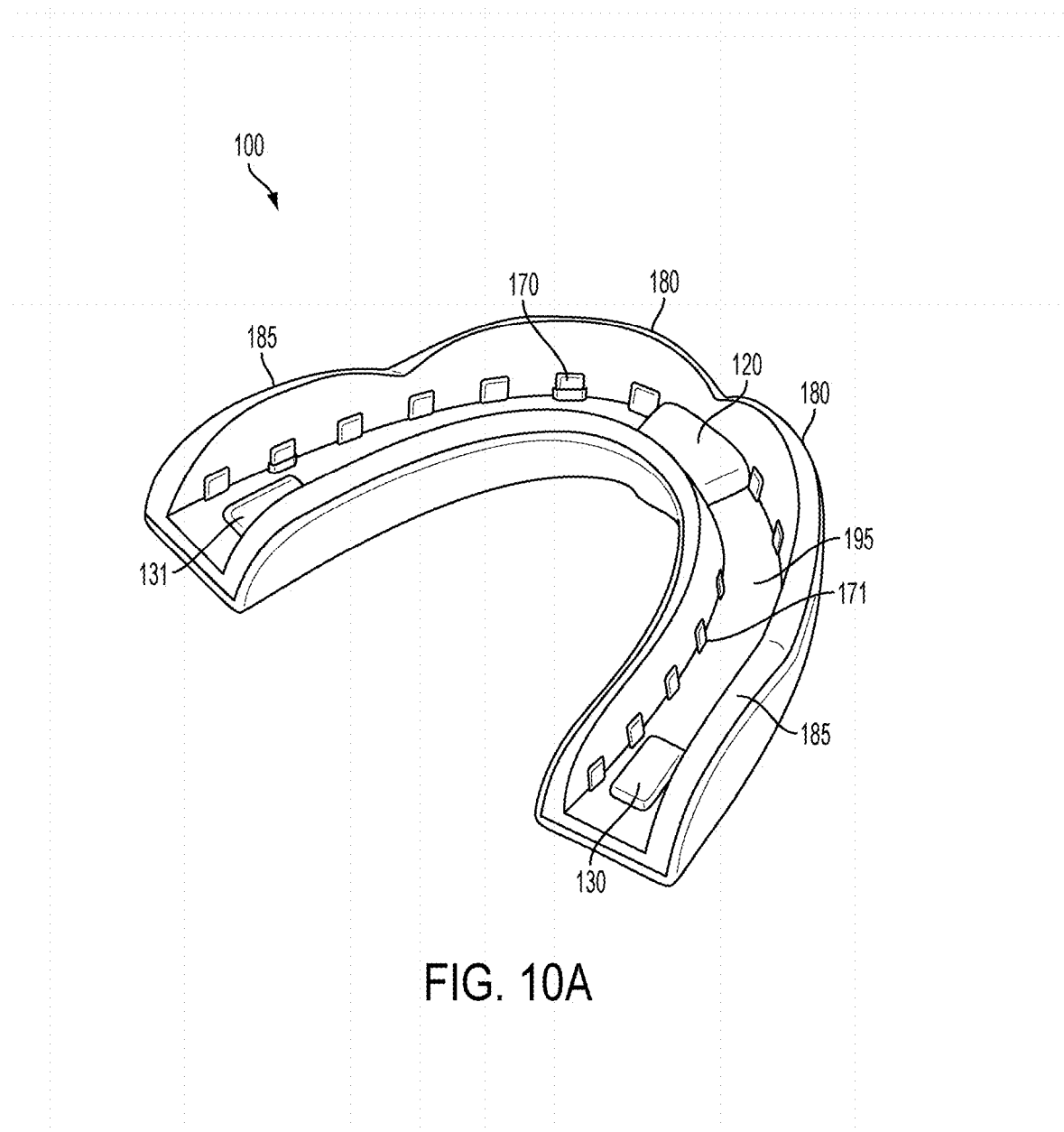

In one or more embodiments, mouthguard 100 includes exoskeleton 110, front internal scaffold 120, rear internal scaffolds 130/131, interior tray portion 140, front exterior scaffold 150, right/left rear outside scaffolds 160/161, exterior bumpers 170, interior bumpers 171, facial flanges 180, buccal flanges 185, interior lingual flange 190, and liner material 195 (see FIG. 10A). The functions and dimensions of these elements will be discussed below.

In an embodiment, the dimensions of rear interior scaffolds 130, 131 may be 10 mm×5 mm in the posterior, and the dimensions of front interior scaffold 120 may be 9.45 mm×12.5 mm with an incisal flare angle $\theta_1=28°$ in the incisal regions. In addition, front/rear interior scaffolds 120/130/131 may be raised to have a height of 3 mm above the bottom of interior tray portion 140 to ensure adequate flow of the flowable liner material 195 when mouthguard 100 is fitted to a user. Rear right/left interior scaffolds 130/131 may be oriented at rear interior scaffold centerline angle $\theta_2=12.5°$. These dimensions should be understood to be exemplary in nature, and not limiting, as other dimensions and/or angles may be determined to be more appropriate for other athletes or user populations.

Figure 4:
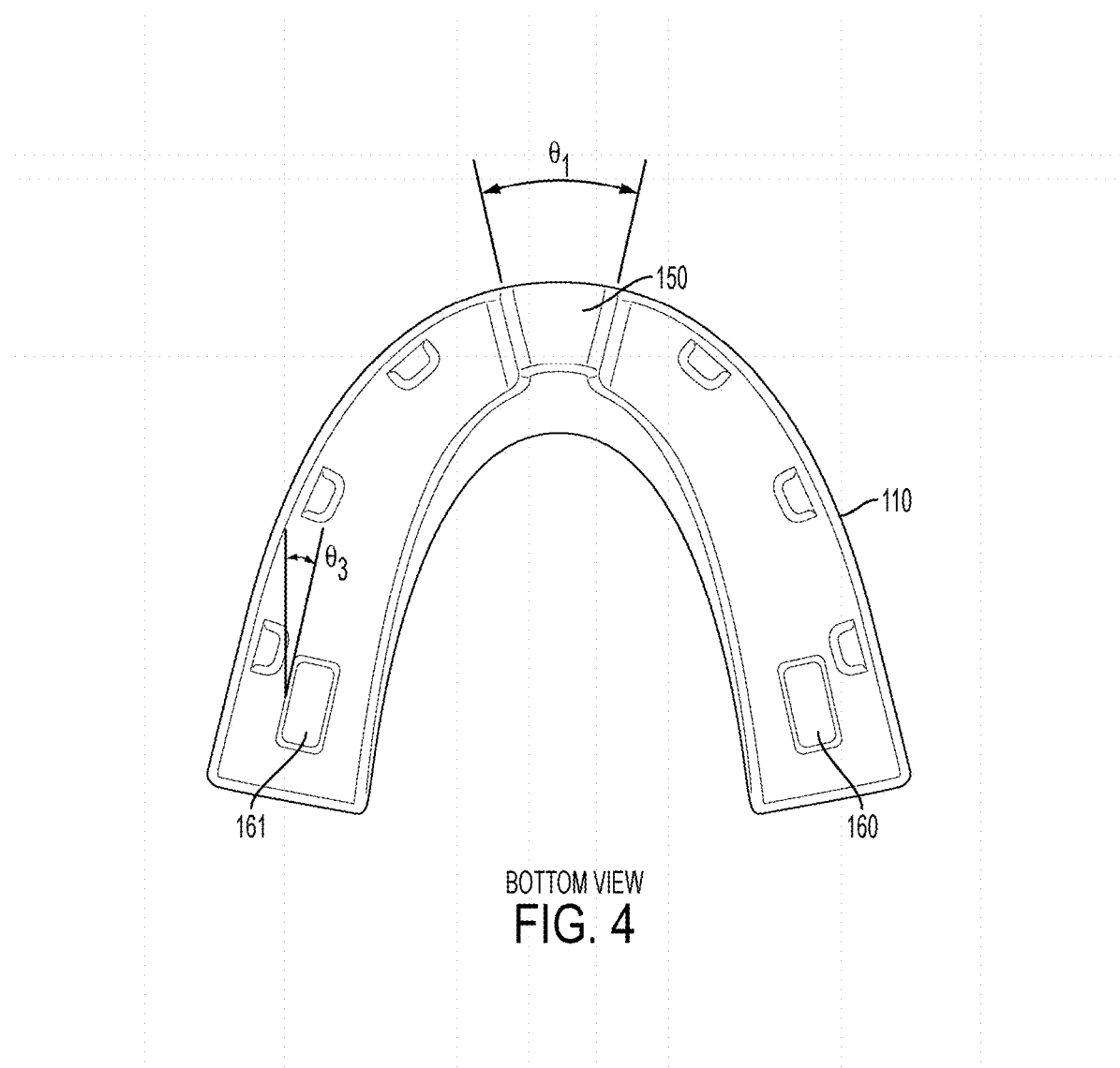
FIG. 4 illustrates a bottom/underside view of the exoskeleton of FIG. 1.

In an embodiment, and as illustrated in the bottom/underside view of FIG. 4, exoskeleton 110 may contain front outside scaffold 150, and right/left rear outside scaffolds 160, 161. It may be appreciated by one of ordinary skill in the art that the front outside scaffold 150 intrinsically functions as an anterior deprogrammer, configured to open a user's bite by an amount associated with the dimensions of the front outside scaffold 150. Rear outside scaffolds 160, 161 may be 1 mm high on the exterior with a determined slant angle $\theta_5$ (see FIGS. 5 and 6). This feature allows the condyle to be positioned in a more downward, anterior position to allow better protection of the TMJ joint and allows the muscle to be placed at a more neutral, relaxed position. For a particular population of users, e.g., NFL® athletes, right/left rear outside scaffold slant angle $\theta_5=3°$ mimics the arc of closure to allow less interference and allows the jaw to be more accurately positioned. These parameters may be adapted for a different population of users.

In one embodiment, facial flanges 180 and buccal flanges 185 of exoskeleton 110 were devised based on the average of scanned models of NFL® athletes and information determined by an interactive user interview process so as to be comfortable but yet protective in design. The average height of facial flanges 180 and buccal flanges 185 is 13.5 mm in one embodiment. These flanges have been determined to allow adequate protection of the teeth and supporting bone and soft tissue from impact. Although the embodiment illustrated is directed to a specific population of athletes, i.e., large adult males who play professional football, the inventive concept described herein is equally applicable to other sports and differently sized athletes, e.g., lacrosse, basketball, wrestling, soccer, judo, etc., without departing from the inventive concept described herein. For example, the various angles, heights, and thicknesses of various components may be separately determined on an average basis for each different athlete population.

In one embodiment, interior lingual flange 190 of exoskeleton 110 was devised using the average height that was deemed comfortable and proper fitting to allow airway exchange and speech for NFL® athletes, but which still provided adequate protection. In one embodiment, the average height of interior lingual flange 190 is 11 mm, with interior lingual flange flare angle $\theta_6=63.4°$. Interior lingual flange 190 allows adequate protection of the teeth and supporting bone and soft tissue from impact. Of course, flare angle $\theta_6$ may (and likely will) be different for a different population of athletes.

Figure 2:
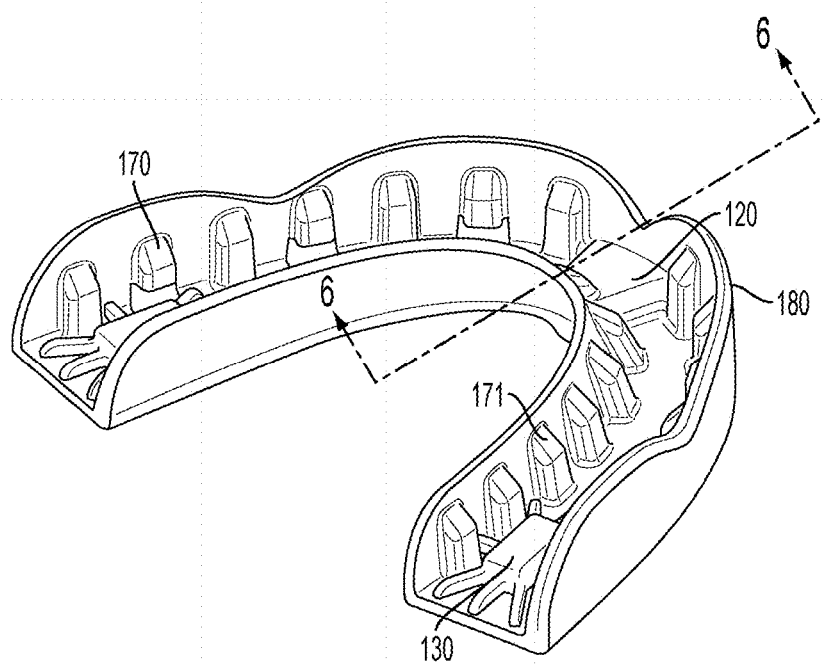
FIG. 2 illustrates a perspective view of the exoskeleton of FIG. 1.
Figure 3:
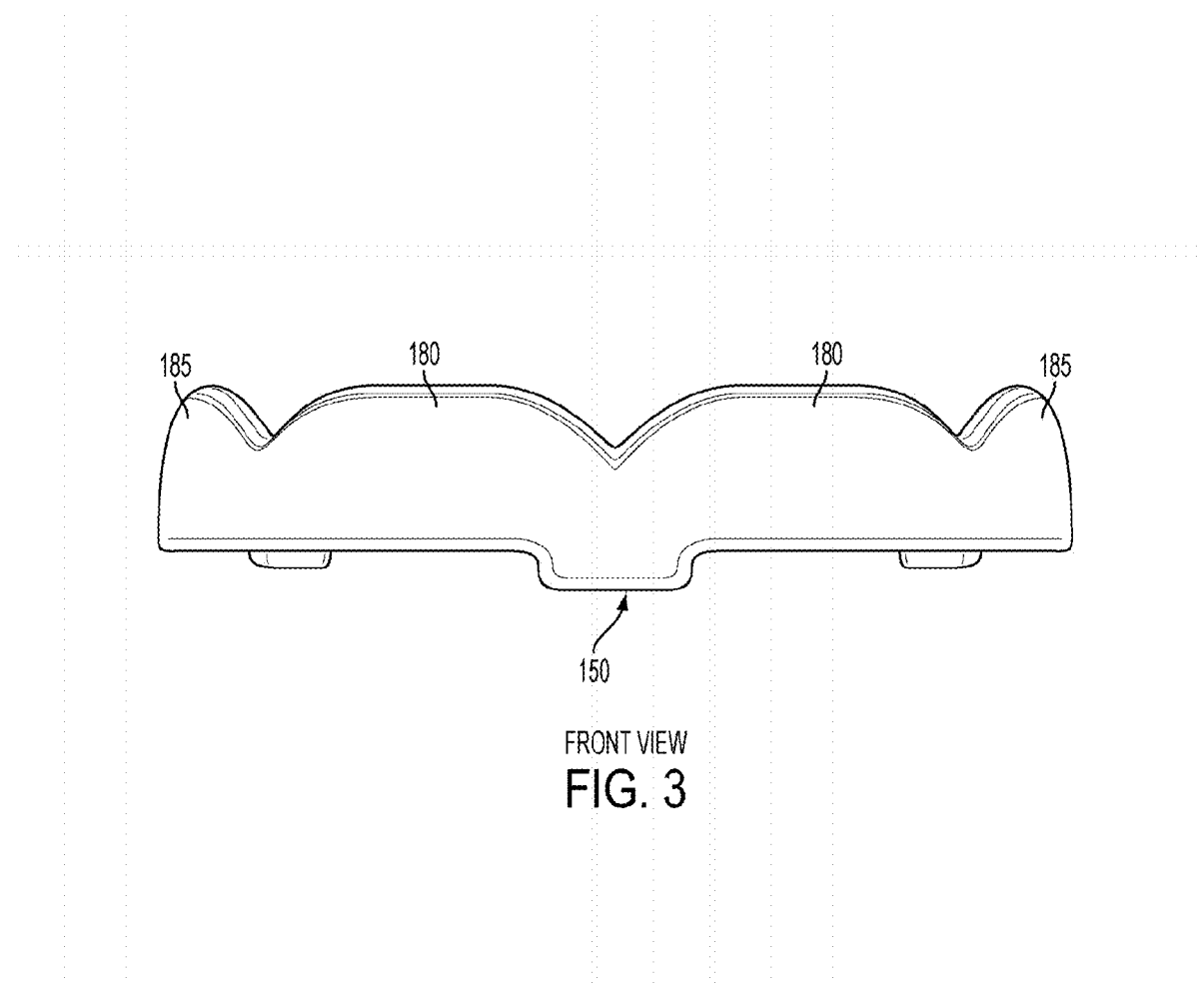
FIG. 3 illustrates a front view of the exoskeleton of FIG. 1.
Figure 5:
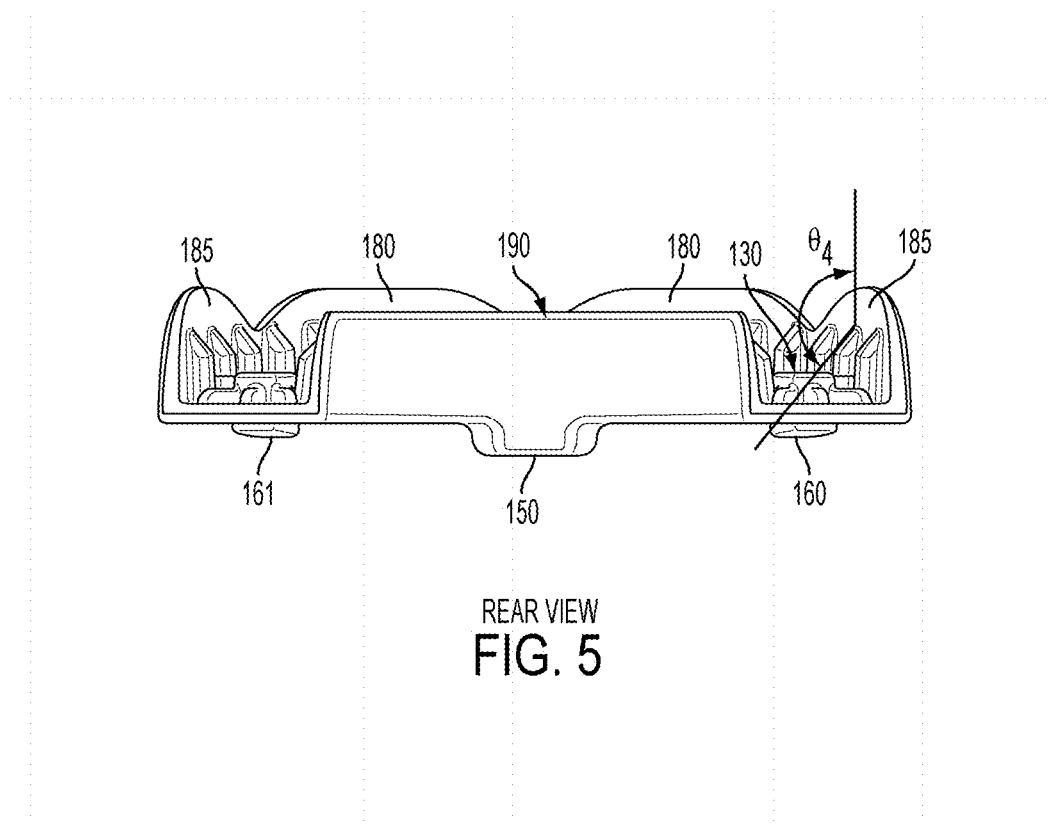
FIG. 5 illustrates a rear view of the exoskeleton of FIG. 1.
Figure 6:
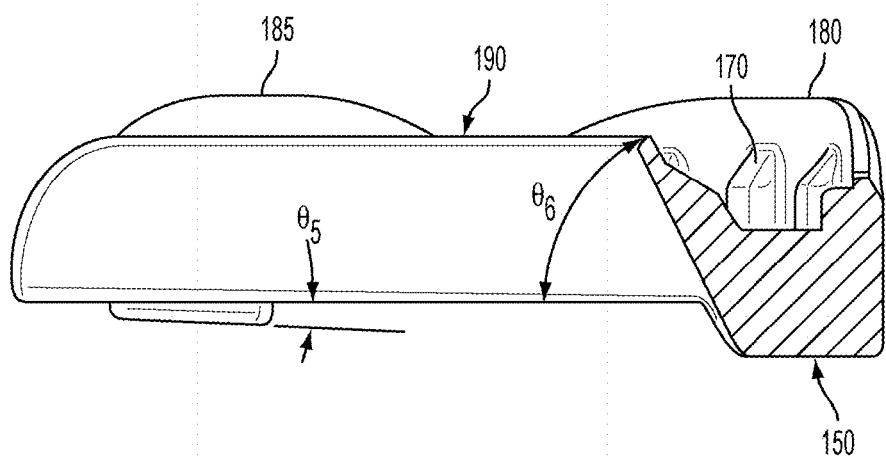
FIG. 6 illustrates a side and partial cutaway sectional view of the exoskeleton of FIG. 1, taken along the sectional line 6-6 of FIG. 2.
Figure 7A:
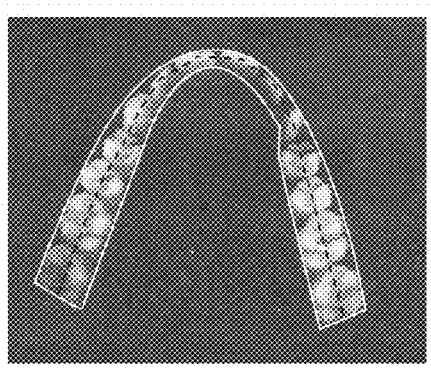
FIGS. 7A through 7E illustrate a representative sample of five patient scan tracings out of a larger patient population used to demonstrate the differences in tooth and jaw alignment between the patients.
Figure 7B:
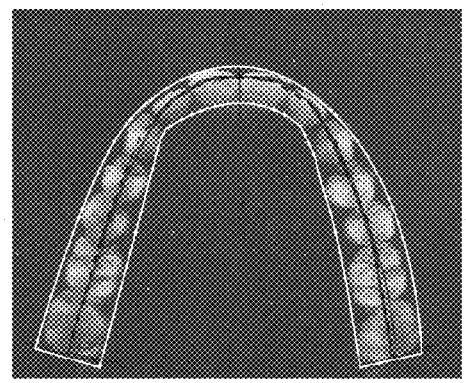
Figure 7C:
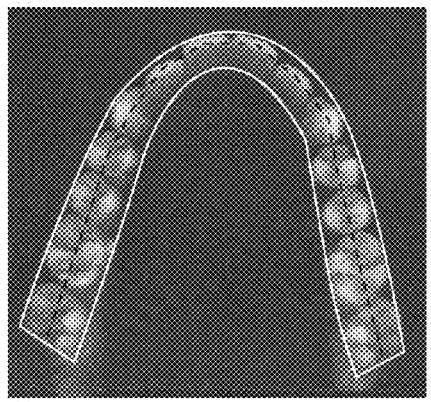
Figure 7D:
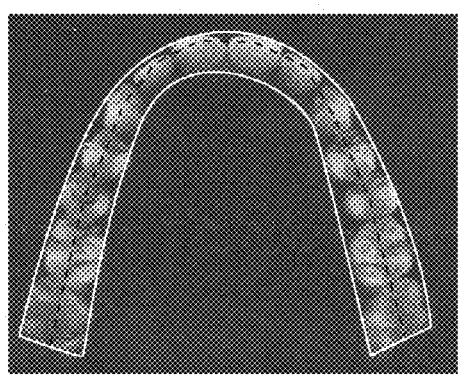
Figure 7E:
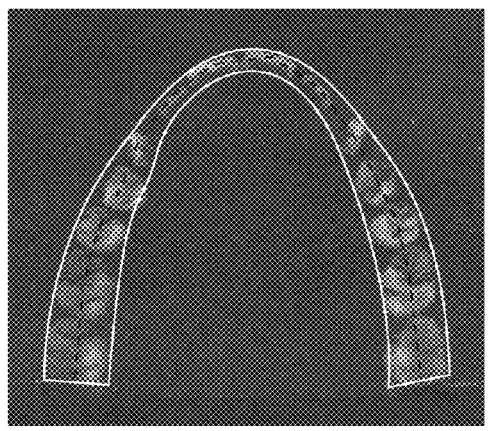

In an embodiment, and as illustrated in FIGS. 1, 2, and 5, for example, exterior bumpers 170 and interior bumpers 171 may project 2 mm from the internal walls to provide an adequate thickness of softening layer for protection, as outlined in the standards set forth by the American Academy of Sports Dentistry. The 2 mm bumper is designed such that the contact surface is generally located at the height of contour of the teeth in contact for the particular athlete population. The 2 mm dimension may be modified for athletes with different average sizes. This ensures sufficient flow of the softer thermoplastic inner layer material, i.e., flowable liner material 195 around each tooth for better protection. In an embodiment, the slope of exterior bumper sidewall angle $\theta_4$, e.g., $\theta_4=45°$ (or $\theta_4=135°$ measured from the vertical sidewall) acts as a guide to properly position mouthguard 100 in the optimally protective position. Mouthguard 100 is centered in order that the impact forces are directed over the long axis of the teeth for better protection. Interior bumpers 171 may be undercut to act as a mechanical lock for flowable liner material 195 to the harder exoskeleton. This reduces the incidence of delamination or separation of the two layers and is an added retention technique in addition to the bond (e.g., chemical and/or mechanical) that joins the two layers of the mouthguard.

In an embodiment, mouthguard 100 may offer advanced dental protection from harmful bacteria by introducing an antimicrobial agent to prevent harmful bacteria from growing inside of the mouthguard. In addition, a Fluoride ($F^-$) leaching material may be provided in the flowable liner material 195 to reduce the carious rate of teeth from the consumption of high sucrose and carbohydrate drinks or performance enhancers commonly consumed by the athletes. provision of a fluoride leaching agent (e.g., in the form of $F^-$) into may help reduce the caries rate by providing protection for the outer enamel matrix of the teeth. Further, the thermoplastic materials used in both exoskeleton 110 and flowable liner material 195 are strong enough to absorb and dissipate forces to reduce traumatic injury to the teeth, TMJ, and surrounding oral structures.

In various embodiments, protective mouthguard 100 may be tethered, e.g., conventional straps may be used to tether the mouthguard to a football helmet mask. However, this approach is generally not preferred for the reasons discussed above. In one embodiment, a ferromagnetic material, e.g., stainless steel or other non-corrosive magnetic material may be embedded in the mouthguard. For example, a magnet and/or ferromagnetic material (not shown) may be embedded in either or both the front and rear scaffolds 120/130/131/150/160/161 of FIG. 1, or both, or in some other location of the outer layer (exoskeleton) such as facial flanges 180. A complementary magnet and/or ferromagnetic material adapted to attract the magnet and/or ferromagnetic material embedded in exoskeleton 110 may be provided separately as a wristband, helmet sticker, or in another suitable location to allow temporary stowage and effective retention of the protective mouthguard when not in use. The present mouthguard design thus provides a novel and breakthrough tethering technique which has long been desired by professional athletes.

The initial fitting operation of a protective mouthguard of an embodiment includes, similar to conventional "boil and bites", heating the protective mouthguard to soften the inner layer, e.g., a thermoplastic layer. The user then places the warmed and softened mouthguard into their mouth, where the tapered and projected side bumpers, acting in cooperation with the front and rear interior scaffolds, and the exterior rear outside scaffolds, ensures proper placement of the mouthguard with respect to the user's teeth, and jaw structure, assuming that the user's pertinent physiological measurements fall within the minimum and maximum averages determined from the measured population.

Such minimum and maximum averages may be determined, for example, from patient populations as represented by the large adult scan tracings of NFL® players in FIG. 7, which is an exemplary subset of a larger sample size. FIG. 8, illustrates the superposition of the five samples that allows determination of an approximate centerline of the five models, along with the maximum and minimum outside dimensions for all five models. Finally, FIG. 9 illustrates a further superposition of the five models to determine a final shape and dimensions of the protective mouthguard. As mentioned above, a larger sample size may be used.

FIGS. 10A through 10H provide various perspective views of an unfitted protective mouthguard of an embodiment. In these figures, flowable liner material 195 is depicted in the lighter shading, and the harder exoskeleton outer layer 110 is depicted by the darker shading. In FIG. 10A, for example, bumpers 170/171 and scaffolds 130/131/160/161 are illustrated.

Figure 10B:
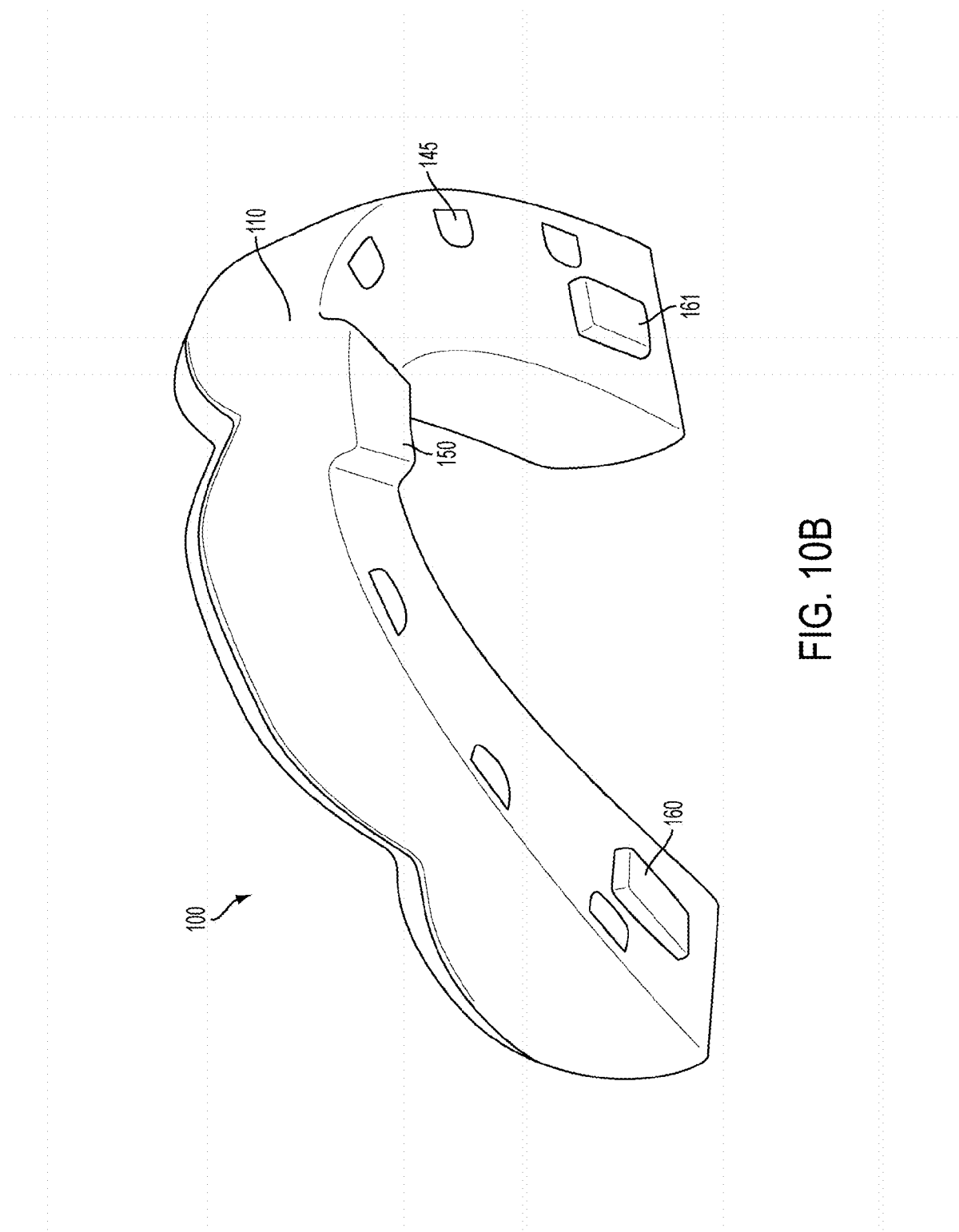
Figure 10C:
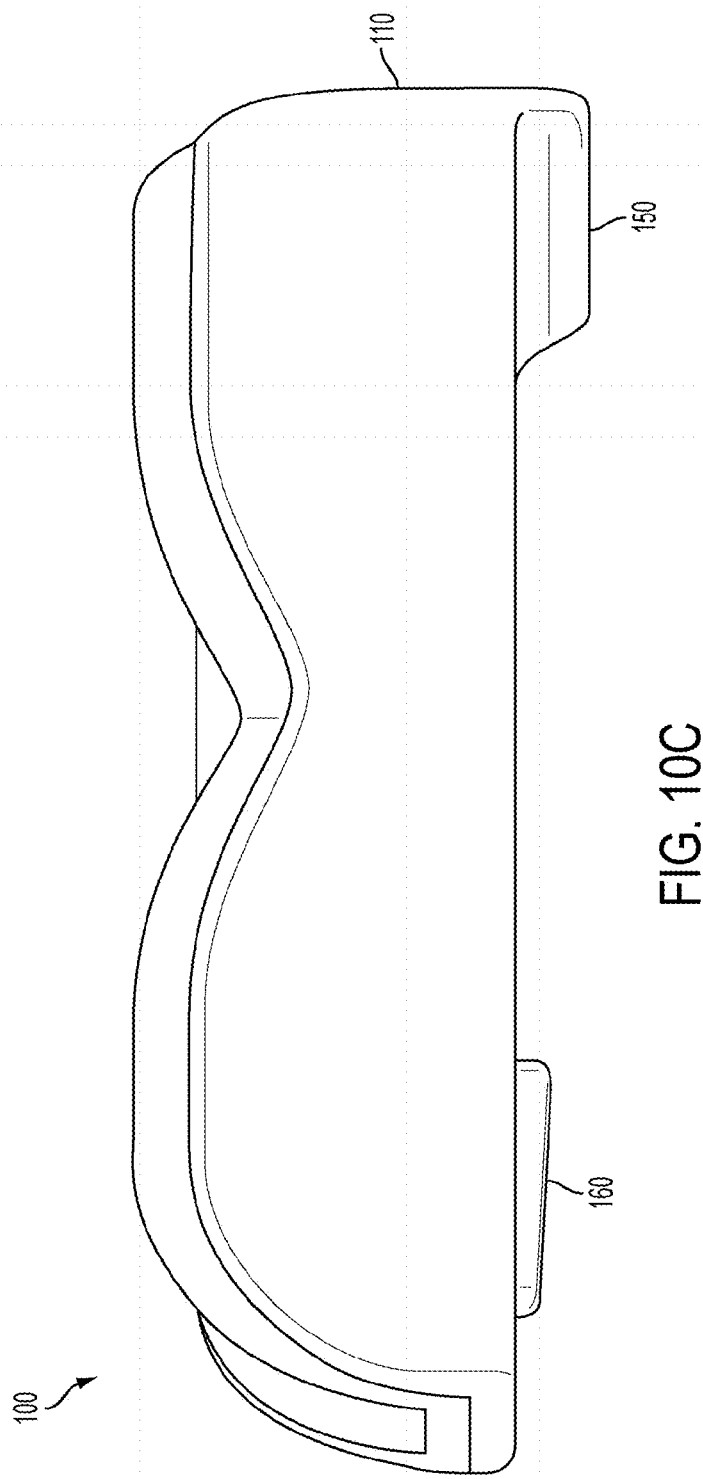
Figure 10D:
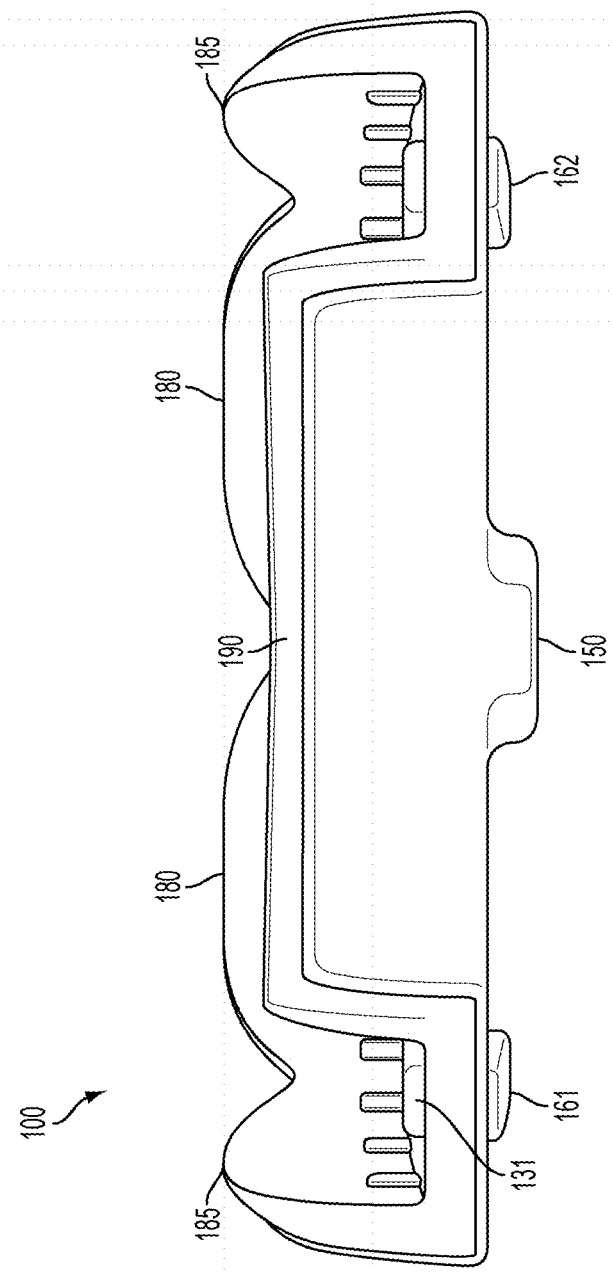
Figure 10E:
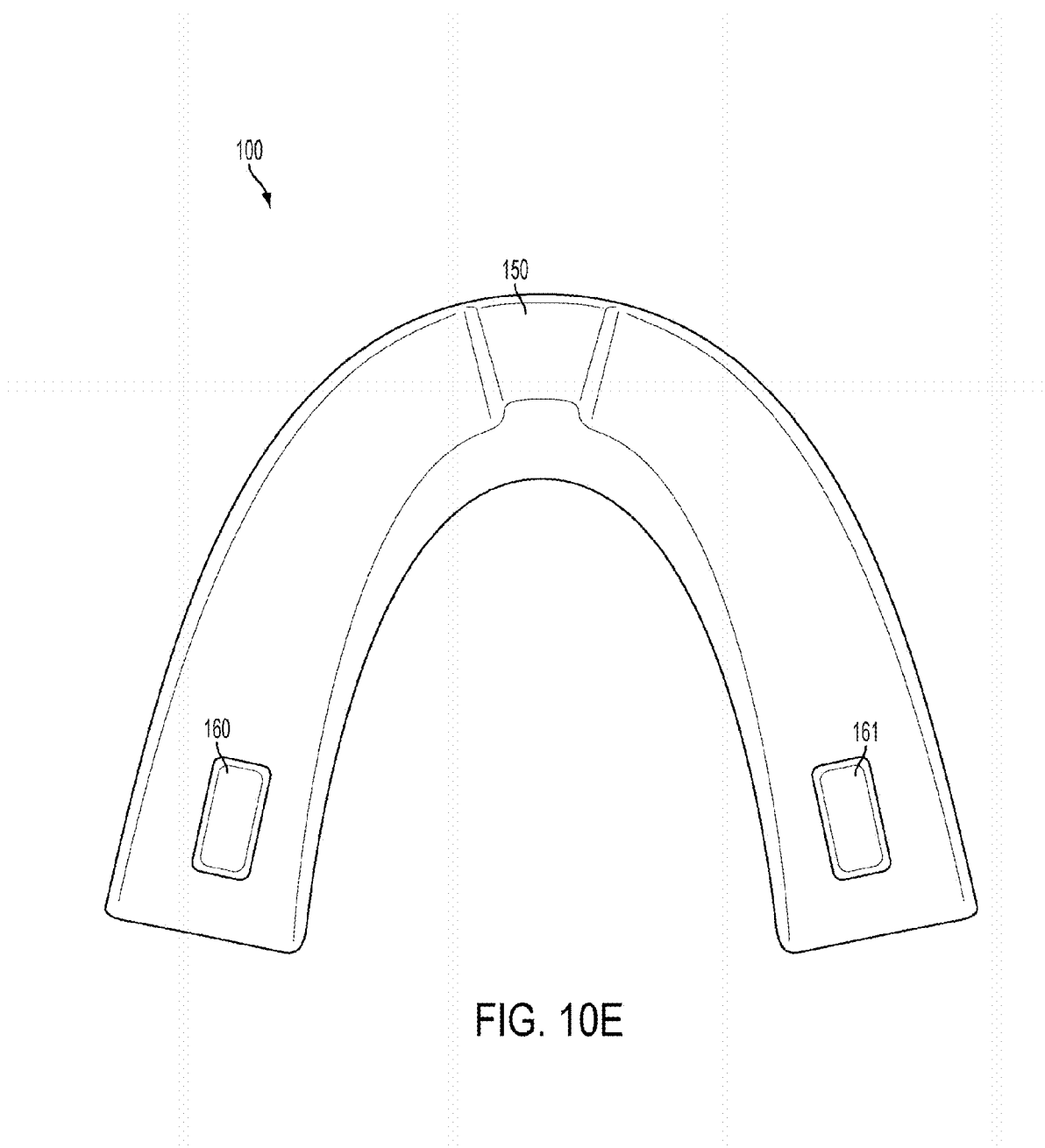
Figure 10F:
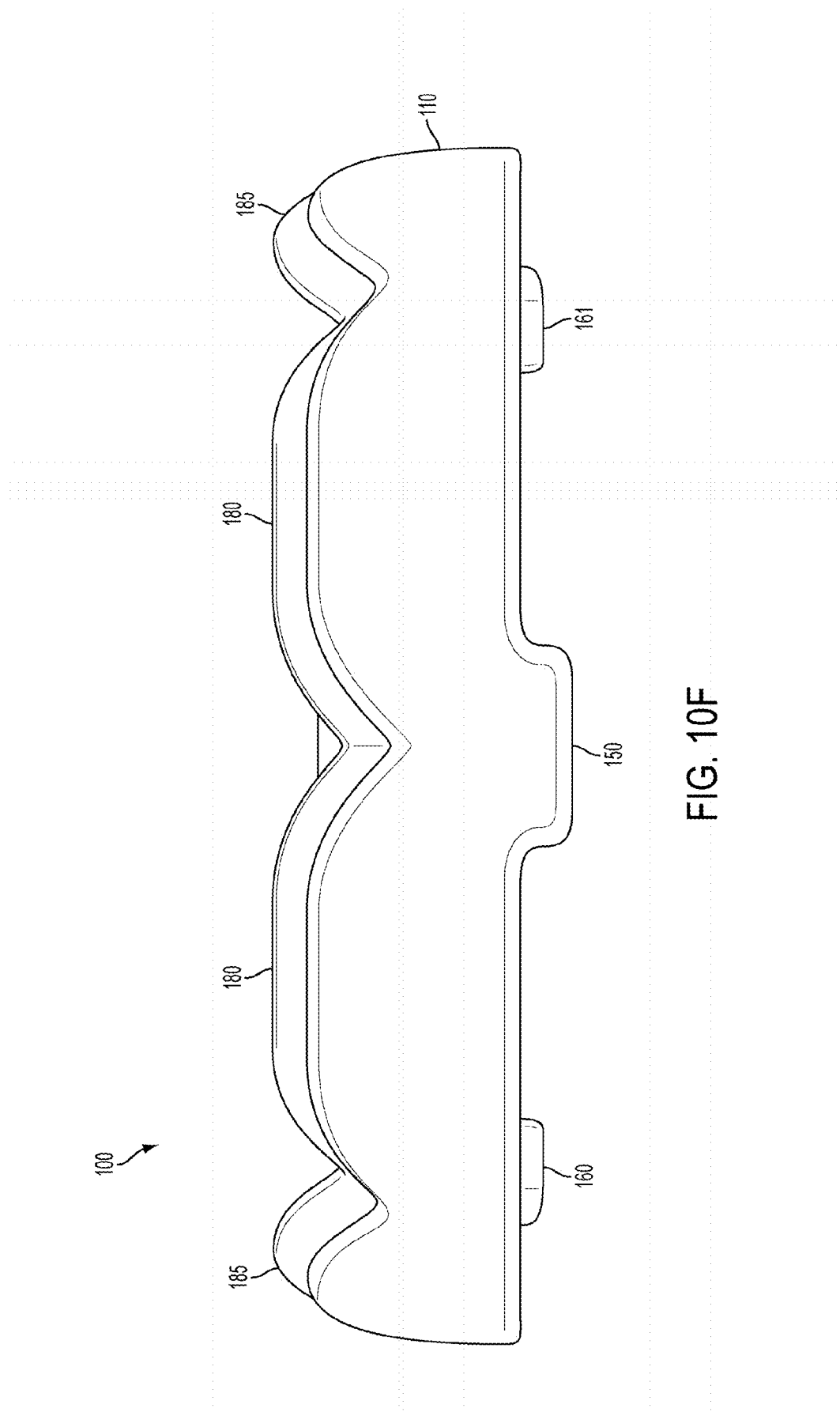
Figure 10G:
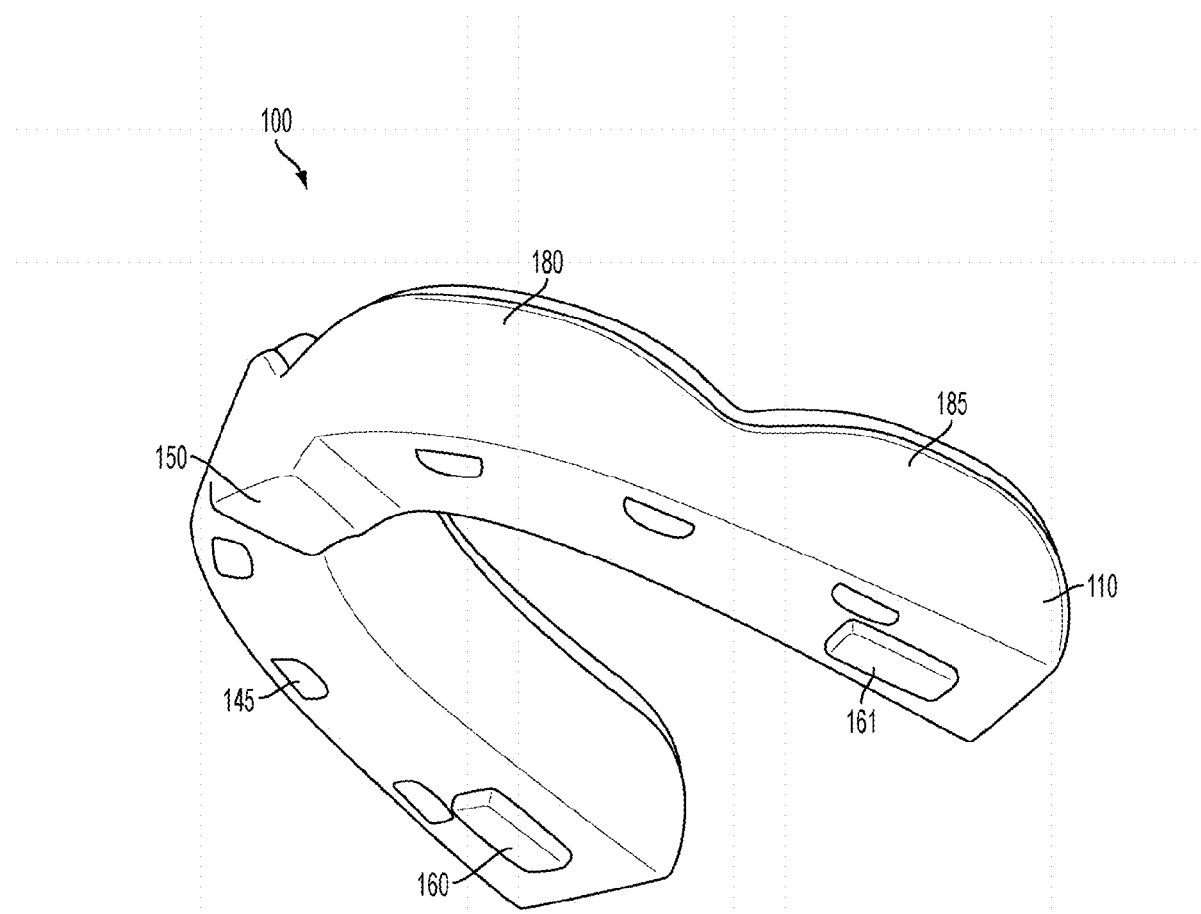
Figure 10H:
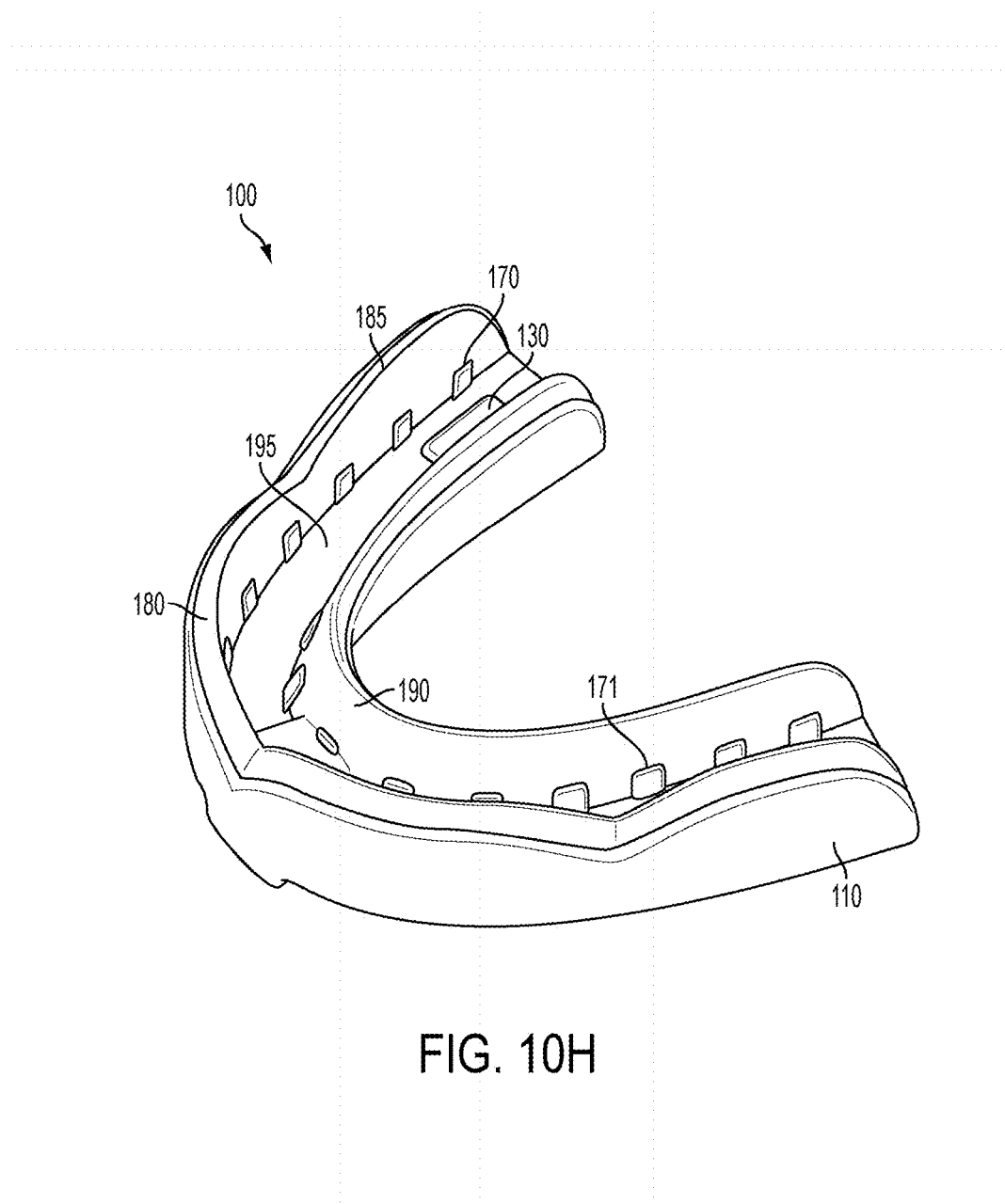

FIGS. 10B and 10G illustrate multiple vent holes 145 in a bottom surface of the mouthguard. These vent holes allow the thermoplastic inner layer material, e.g., EVA material, to flow out of the tray portion of the mouthguard when the mouthguard is being fitted over the upper teeth of the user. The inner layer material that flows out the vent holes may aid in cushioning the bottom teeth.

Fitting such a mouthguard to a patient may be accomplished in various ways. For example, the inner layer may be heated and softened, and then placed in contact with the oral structures in the patient's mouth, similar to conventional "boil and bites, with the notable exception of the improved fit and performance achieved by the use of the novel exoskeleton and associated features of this disclosure. Alternatively, with the advent of digital scanning technology, accurate models of the patient's oral structures can be obtained using a digital camera, and a plaster or stone model can be cast based upon the digital image(s). The resulting cast model can be used to preform the mouthguard described above, thus providing valuable customer service by having the ability to fit mouthguards to patients that are not physically present in the dentist's office.

Turning now to FIG. 11, clamp mechanism 200 includes T-nut 210, first clamp half 220, second clamp half 221, screw 240, ferrous/magnetic material 250, ferrous/magnetic material receiver or opening 251, and protective covering 260. Ferrous/magnetic material 250 may be ferrous material if mouthguard 100 includes an embedded magnet, or it may be magnetic material if mouthguard 100 includes an embedded piece of ferrous material, or both ferrous/magnetic material 250 and mouthguard 100 may include magnetic material, as long as there is magnetic attraction between the elements to ensure proper retention force and stowage. When assembled, first clamp half 220 and second clamp half 221 clamp around facemask bar 230, and are retained in position by the interaction between screw 240 and T-nut 210. As should be appreciated, facemask bar 230 does not form part of the inventive concept, but merely illustrates one environment of use of clamp mechanism 200.

Turning now to FIGS. 12A-12D, an alternative clamp mechanism 300 includes first clamp half 320, second clamp half 330, lock detents 331/332, screw 340, ferrous/magnetic material 350, ferrous/magnetic material receiver or opening 355, protective latching cover 360, and lock mechanism 361. Although not shown, alternative clamp mechanism 300 may also include a T-nut to receive screw 340 as in clamp mechanism 200.

First clamp half 320 and second clamp half 330 of alternative clamp mechanism 300 may assemble around a facemask bar similarly to first clamp half 220 and second clamp half 221 of clamp mechanism 200, but protective latching cover 360 attaches in a different manner and more securely by the use of lock mechanism 361 in cooperation with lock detents 331/332. Lock detents 331/332 are made of a plastic material, and their design allows flexure in an inward direction to engage lock mechanism 361, as illustrated in FIG. 12D.

Turning now to FIGS. 13A-13B, another alternative clamp mechanism 400 includes T-nut 410, first clamp half 420, second clamp half 430, latches 431, screw 440, ferrous/magnetic material 450, and protective latching ring 460. Similar to other embodiments, alternative T-nut 410 receives screw 440 to hold clamp mechanism 400 in an assembled condition. In addition, facemask bar groove 470 may be arranged in one or more of first clamp half 420 and second clamp half 430 to receive, for example, a bar of a facemask.

Although similar in some respects to other embodiments, protective latching ring 460 attaches in a different manner by the use of latches 431 around latching ring 460 and which may be made of a plastic material, but which requires less plastic to reduce weight and cost, for example.

It should be noted that the disclosure above mentions various dimensions and angles of various components, but these measurements are not to be construed as limiting, as they merely represent an example of measurements for a particular group and/or type/size of athlete. Other groups, types and/or sizes of athletes may have different dimensions and attributes which may be determined by measuring and averaging techniques.

The above-discussed embodiments and aspects of this disclosure are not intended to be limiting, but have been shown and described for the purposes of illustrating the functional and structural principles of the inventive concept, and are intended to encompass various modifications that would be within the spirit and scope of the following claims.

List of Reference Numbers

Table 1 below lists reference numbers utilized in the specification and drawings:

TABLE 1

| Ref. No. | Description |
| --- | --- |
| 100 | mouthguard |
| 110 | outer core/exoskeleton |
| 120 | front interior scaffold |
| 130 | right rear interior scaffold |
| 131 | left rear interior scaffold |
| 140 | interior tray portion |
| 145 | multiple vent holes |
| 150 | front outside scaffold |
| 160 | right rear outside scaffold |
| 161 | left rear outside scaffold |
| 170 | exterior bumpers |
| 171 | interior bumpers |
| 180 | facial flanges |
| 185 | buccal flanges |
| 190 | interior lingual flange |
| 195 | flowable liner material |
| 200 | clamp mechanism |
| 210 | T-nut |
| 220 | first clamp half |
| 221 | second clamp half |
| 230 | facemask bar |
| 240 | screw |
| 250 | ferrous/magnetic material |
| 251 | ferrous/magnetic material receiver or opening |
| 260 | protective covering |
| 300 | alternative clamp mechanism |
| 320 | first clamp half |
| 330 | second clamp half |
| 331 | lock detent |
| 332 | lock detent |

TABLE 1-continued

| Ref. No. | Description |
| --- | --- |
| 340 | screw |
| 350 | ferrous/magnetic material |
| 355 | ferrous/magnetic material receiver or opening |
| 360 | protective latching cover |
| 361 | lock mechanism |
| 400 | alternative clamp mechanism |
| 410 | T-nut |
| 420 | first clamp half |
| 430 | second clamp half |
| 431 | latch |
| 440 | screw |
| 450 | ferrous/magnetic material |
| 460 | protective latching ring |
| 470 | facemask bar groove |
| $\theta_1$ | incisal flare angle |
| $\theta_2$ | rear interior scaffold centerline angle |
| $\theta_3$ | rear outside scaffold centerline angle |
| $\theta_4$ | exterior bumper sidewall angle |
| $\theta_5$ | right/left rear outside scaffold slant angle |
| $\theta_6$ | interior lingual flange flare angle |

What is claimed is:

1. A dual layer protective mouthguard, comprising:
an outer layer comprising an exoskeleton having a generally U-shaped tapered base and inner and outer walls adapted to extend into a vestibular area of an oral cavity of a particular person using the protective mouthguard;
an inner layer comprising a material laminated with the inner wall of the outer layer,
wherein the exoskeleton comprises front and rear interior scaffold structures having a predetermined height above a bottom of the U-shaped tapered base selected to contact incisor and molar teeth of a selected population of users using the protective mouthguard so as to ensure a uniform thickness of the inner layer material when the protective mouthguard has been fitted to the particular person in the selected population of users,
wherein the exoskeleton further comprises interior tapered side bumpers extending from the interior wall of the exoskeleton, said interior tapered side bumpers arranged to position the mouthguard within the oral cavity and provide a plurality of contact surfaces located at a contour height suitable for contacting teeth of the selected population of users, said plurality of contact surfaces ensuring a desired flow of the inner layer material around each tooth of the particular person when the mouthguard is being fitted to the particular person and thereby provide a desired protective thickness of the inner layer material after being fitted.

2. The mouthguard of claim 1, wherein the predetermined height of one or more of the front and rear interior scaffolds is 3 mm.

3. The mouthguard of claim 1, wherein the interior tapered side bumpers extend 2 mm from the interior wall of the exoskeleton.

4. The mouthguard of claim 1, wherein the interior tapered side bumpers are tapered at an angle of 45 degrees with respect to the interior wall of the exoskeleton.

5. The mouthguard of claim 1, wherein the interior tapered side bumpers are arranged so as to align the mouthguard in the oral cavity such that impact forces are directed over a long axis of said each tooth of the particular user.

6. The mouthguard of claim 1, wherein a flare of the front interior scaffold is 28 degrees in incisal regions thereof.

7. The mouthguard of claim 1, further comprising rear outside scaffolds arranged at a predetermined angle with respect to a longitudinal axis of the protective mouthguard so as to allow a condyle of the particular person to be positioned in a downward, anterior position so as to protect a TMJ joint thereof and to provide an arc of closure to reduce interference and allow accurate position of a jaw of the particular person.

8. The mouthguard of claim 7, wherein the predetermined angle is 3 degrees.

9. The mouthguard of claim 1, further comprising facial and buccal flanges having an average height determined from an average of the selected population of users and selected so as to provide desired protection from impact of teeth, supporting bone, and soft tissue of the particular person.

10. The mouthguard of claim 9, wherein the average height is 13.5 mm.

11. The mouthguard of claim 1, further comprising an interior lingual flange having an average height determined from an average of the selected population of users and having a flare angle selected so as to provide desired protection from impact of teeth, supporting bone, and soft tissue of the particular person, as well as a desired airway exchange and speech of the particular person.

12. The mouthguard of claim 11, wherein the average height is 11 mm.

13. The mouthguard of claim 11, wherein the flare angle is 63.4 degrees.

14. The mouthguard of claim 1, wherein one or more of the interior tapered side bumpers are undercut so as to provide a mechanical joint between the laminated inner and outer layers, said mechanical joint providing a mechanical bond between the inner and outer layers to thereby prevent delamination thereof.

15. The mouthguard of claim 1, wherein the inner layer is chemically bonded to the outer layer.

16. The mouthguard of claim 15, wherein the inner layer is mechanically coupled to the outer layer.

17. The mouthguard of claim 1, wherein the exoskeleton comprises a first magnetic and/or ferromagnetic material embedded therein,
    said first magnetic and/or ferromagnetic material being arranged to cooperate with an external attachment mechanism having a second magnetic and/or ferromagnetic material therein, said first and second materials being selected in combination so as to provide a magnetic attraction force therebetween.

18. The mouthguard of claim 17, wherein said external attachment mechanism is selected from the group consisting of: a mechanical attachment to a helmet, a decal suitable for attachment to a helmet, and a wristband.

19. The mouthguard of claim 1, wherein the inner layer is selected to have mechanical properties suitable for absorbing and dissipating external forces so as to prevent injury to the teeth, TMJ, and surrounding oral structures of the particular person.

20. The mouthguard of claim 1, wherein the inner layer comprises an antimicrobial material selected to at least reduce bacteria harmful to humans.

21. The mouthguard of claim 1, wherein the inner layer comprises a cavity reducing material selected to at least reduce a carious rate of any teeth in contact with the inner layer.

22. The mouthguard of claim 21, wherein the cavity reducing material comprises a Fluoride ($F^-$) leaching material.

23. The mouthguard of claim 1, wherein the inner layer comprises a thermo-plastic flowable material.

24. The mouthguard of claim 1, wherein the inner layer comprises either a polystyrene material, an EVA material, or a blend thereof.

25. The mouthguard of claim 1, wherein the inner layer comprises a nanocarbon fiber material.

26. The mouthguard of claim 25, wherein the nanocarbon fiber material is embedded in a flowable material to provide support for the inner layer.

27. The mouthguard of claim 1, wherein the outer layer comprises a nanocarbon fiber material.

28. A mouthguard tethering system comprising the mouthguard of claim 17, said external attachment mechanism comprising a clamp mechanism,
    wherein said clamp mechanism comprises:
        a first clamp half;
        a second clamp half;
        a connector arrangement configured to connect the first clamp half to the second clamp half;
        a ferrous and/or magnetic disc configured to be received in an opening in the second clamp half; and
        a protective covering arranged to cover the connector arrangement, the ferrous and/or magnetic disc and the opening in the second clamp half.

29. The mouthguard tethering system of claim 28, wherein the second clamp half comprises a lock detent mechanism configured to lock the protective covering to the second clamp half.

30. The mouthguard tethering system of claim 28, wherein the ferrous and/or magnetic disc is selected to cooperate with said first magnetic and/or ferromagnetic material in the mouthguard so as to provide a magnetic attraction force therebetween sufficient to hold the mouthguard to the protective covering.

31. A method of fitting the protective mouthguard of claim 1 to a particular person having physiological parameters encompassed by the selected population of users, the method comprising:
    heating the inner layer;
    placing the protective mouthguard including the heated inner layer in the oral cavity of the particular person using the protective mouthguard;
    contacting the front and rear interior scaffold structures with incisor and molar teeth of the particular person and thereby ensuring a uniform thickness of the inner layer material;
    using the interior tapered side bumpers to position the mouthguard within the oral cavity and thereby provide a plurality of contact surfaces and thereby ensuring a desired flow of the inner layer material around each tooth of the particular person;
    forming the protective mouthguard to oral structures of the particular person,
    said interior tapered side bumpers and said front and rear interior scaffold structures ensuring a desired protective thickness of the inner layer material after the heated inner layer has cooled, said interior tapered side bumpers ensuring aligning the mouthguard in the oral cavity such that impact forces are directed over a long axis of each tooth of the particular user.

32. A method of fitting the protective mouthguard of claim 1 to a particular person having physiological parameters encompassed by the selected population of users, the method comprising:
    obtaining a digitally scanned image of oral structures of the particular person;
    using the digitally scanned image to form a model of the oral structures;
    heating the inner layer;
    preforming the protective mouthguard to a shape of the oral structures by using the model, said interior tapered side bumpers and said front and rear interior scaffold structures ensuring a desired protective thickness of the inner layer material after the heated inner layer has cooled, said interior tapered side bumpers ensuring aligning the mouthguard in the oral cavity such that impact forces are directed over a long axis of each tooth of the particular user.

* * * * *